United States Patent
Brown et al.

(10) Patent No.: US 6,494,914 B2
(45) Date of Patent: Dec. 17, 2002

(54) UNICONDYLAR FEMORAL PROSTHESIS AND INSTRUMENTS

(75) Inventors: David Ray Brown, Warsaw; Jacy Charles Hoeppner, Syracuse, both of IN (US)

(73) Assignee: Biomet, Inc., Warsaw, IN (US)

( * ) Notice: Subject to any disclaimer, the term of this patent is extended or adjusted under 35 U.S.C. 154(b) by 0 days.

(21) Appl. No.: 09/730,264

(22) Filed: Dec. 5, 2000

(65) Prior Publication Data

US 2002/0068979 A1 Jun. 6, 2002

(51) Int. Cl.$^7$ .................................................. A61F 2/38
(52) U.S. Cl. ................. 623/20.3; 623/20.14; 623/20.15
(58) Field of Search ............................. 623/20.3, 20.31, 623/20.14, 20.15, 20.16

(56) References Cited

U.S. PATENT DOCUMENTS

| | | | |
|---|---|---|---|
| 3,715,763 A | | 2/1973 | Link |
| 3,774,244 A | * | 11/1973 | Walker ..................... 623/20.3 |
| 3,852,830 A | | 12/1974 | Marmor |
| 4,085,466 A | * | 4/1978 | Goodfellow et al. ........ 623/20.3 |
| 4,355,429 A | * | 10/1982 | Mittelmeier et al. ...... 623/20.14 |
| 4,838,891 A | | 6/1989 | Bränemark et al. |
| 4,911,721 A | | 3/1990 | Bränemark et al. |
| 5,207,711 A | | 5/1993 | Caspari et al. |
| 5,226,915 A | * | 7/1993 | Bertin ......................... 623/20 |
| 5,258,032 A | | 11/1993 | Bertin |
| 5,314,482 A | | 5/1994 | Goodfellow et al. |
| 5,445,642 A | | 8/1995 | McNulty et al. |
| 5,486,176 A | | 1/1996 | Hodge |
| 5,562,675 A | | 10/1996 | McNulty et al. |
| 5,624,444 A | | 4/1997 | Wixon et al. |
| 5,688,280 A | | 11/1997 | Booth, Jr. et al. |
| 5,702,459 A | | 12/1997 | Hummer et al. |
| 5,776,137 A | | 7/1998 | Katz |

FOREIGN PATENT DOCUMENTS

WO     WO90/14806     12/1990

OTHER PUBLICATIONS

"The Oxford Phase 3 Unicompartmental Knee—Manual of the Surgical Technique" (advertising brochure), published by Biomet/Merck (date unknown).
"Miller/Galante Unicompartmental Knee—System Implants and Instrumentation" (advertising brochure), published by Zimmer (date unknown).
"Miller/Galante Unicompartmental Knee—System Surgical Technique" (advertising brochure), published by Zimmer (date unknown).
"Genus Uni Knee System Technique"—Surgical Technique by Jonathan Braslow, M.D. (advertising brochure), published by Biomet in 1998.

* cited by examiner

Primary Examiner—Corrine McDermott
Assistant Examiner—Alvin Stewart
(74) Attorney, Agent, or Firm—Harness, Dickey & Pierce, P.L.C.

(57) ABSTRACT

A set of femoral orthopedic devices includes a first component having a first size and a second component having a second size. The first component includes a peg positioned a predetermined distance from a first reference point The second component includes a peg positioned said predetermined distance from said first reference point. The method calls for referencing a femoral condyle at a first reference point, locating a peg aperture a predetermined distance from the first reference point, selecting a sized femoral component, and implanting the femoral component. The size of the femoral component is defined by a distance from the peg to a second reference point.

20 Claims, 6 Drawing Sheets

UNICONDYLAR FEMORAL PROSTHESIS AND INSTRUMENTS

BACKGROUND AND SUMMARY OF THE INVENTION

The present invention relates generally to prosthesis and instruments used during knee surgery for the reinstatement of the natural knee joint. More particularly, the invention relates to a unicondylar femoral prosthesis and the instruments used to properly size and locate the prosthesis using anterior or posterior referencing.

For various reasons, the human knee fails at the tibial and femoral juncture causing great pain and suffering to the individual. To correct this problem, surgeons now replace all or part of the natural knee joint with artificial components. In one type of partial knee replacement, an artificial tibial component is placed on the proximal end of the tibia and an artificial femoral component is placed on the distal end of the femur.

Because each individual's femur and tibia are different in size and because the extent of damage to the tibia and femur ends cannot accurately be determined until after the knee has been opened by the surgeon, the size of the implant components cannot be easily determined prior to the operation. Accordingly, it is common practice to initiate the operation, open up the knee, fully evaluate the needs of the patient and, at that time, determine the size of the femoral and tibial components required. In view of this practice, manufacturers of femoral and tibial components typically manufacture five to eight different size component sets to be available to the surgeon during the operation.

Additionally, once the knee is open, the surgeon evaluates the patient to determine which of two referencing methods will best suit the patient. In anterior referencing, careful attention is given to the patellofemoral joint by using an anteriorally placed feeler gage. This referencing system focuses on allowing proper ligament balance and stability in extension as well as consistent patellofemoral placement on the anterior surface.

A second type of instrument design (posterior referencing) is based on the concept that flexion and extension stability are more important than the patello transition location. Specifically, the flexion gap is better balanced to avoid laxity in flexion or tightness in flexion.

In the case of sizing the femoral distal end in determining which of the femoral component sizes to use, the common practice has been to measure the anterior to posterior distance of the femur and, utilizing this measurement, to pick an appropriate size femoral component. Unfortunately, this technique is relatively invasive because the instrument used to measure the anterior to posterior femoral distal end distance is relatively large and unwieldy.

Many surgeons wishing to avoid patient morbidity associated with the aforementioned invasive procedure have chosen an instrument free method of resection. In this method, the surgeon removes portions of the femoral distal end with a burr operated by hand without the use of a resection guide. While such a method is less invasive, the resected surface created by the burr is not accurately located relative to a reference point. Unfortunately, variation in the final positioning of the femoral component occurs.

Accordingly, an object of the present invention is to provide a method and apparatus enabling implantation of a unicondylar femoral prosthesis with minimal bone removal.

Another object of the present invention is to provide a minimally invasive technique for producing reproducible bone resections using either anterior or posterior referencing.

The present invention relates to a set of femoral orthopedic devices and a method of implanting the devices. The set of femoral orthopedic devices includes a first component having a first size and a second component having a second size. The first component includes a peg positioned a predetermined distance from a first reference point The second component includes a peg positioned a predetermined distance from said first reference point. The method calls for referencing a femoral condyle at a first reference point, locating a peg aperture a predetermined distance from the first reference point, selecting a sized femoral component, and implanting the femoral component. The size of the femoral component is defined by a distance from the peg to a second reference point.

BRIEF DESCRIPTION OF THE DRAWINGS

The various advantages of the present invention will become apparent to one skilled in the art by reading the following specification and subjoined claims and by referencing the following drawings in which:

DETAILED DESCRIPTION OF THE PREFERRED EMBODIMENT

The following description of the preferred embodiments concerning a unicondylar femoral prosthesis and instruments are merely exemplary in nature and are not intended to limit the invention or its application or uses. Moreover, while the present invention is described in detail below with respect to a right medial unicondylar prosthesis, it will be appreciated by those skilled in the art that the present invention may be applied to various other types of knee joint prostheses such as a total knee joint prosthesis.

Figure 1:
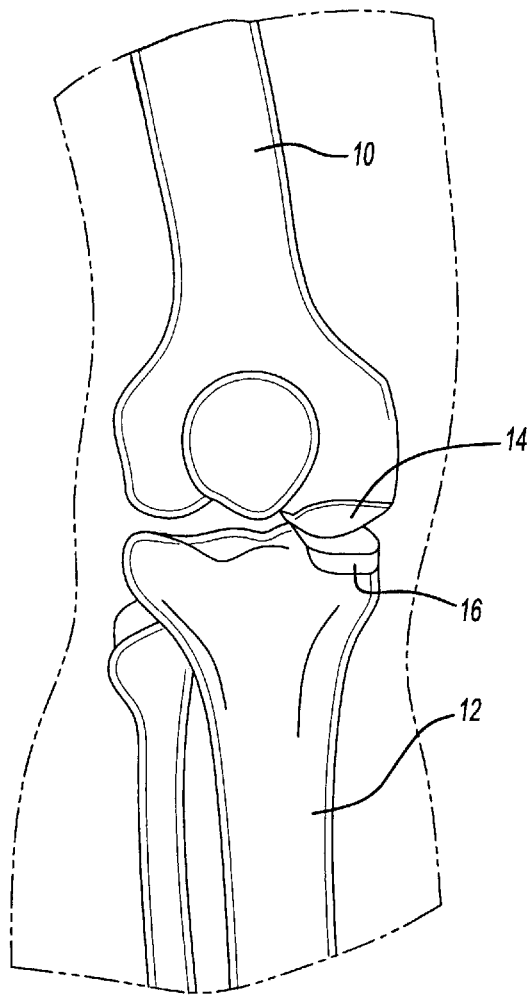
FIG. 1 is an anterior view of an embodiment of the present invention implanted in a knee joint.
Figure 2:
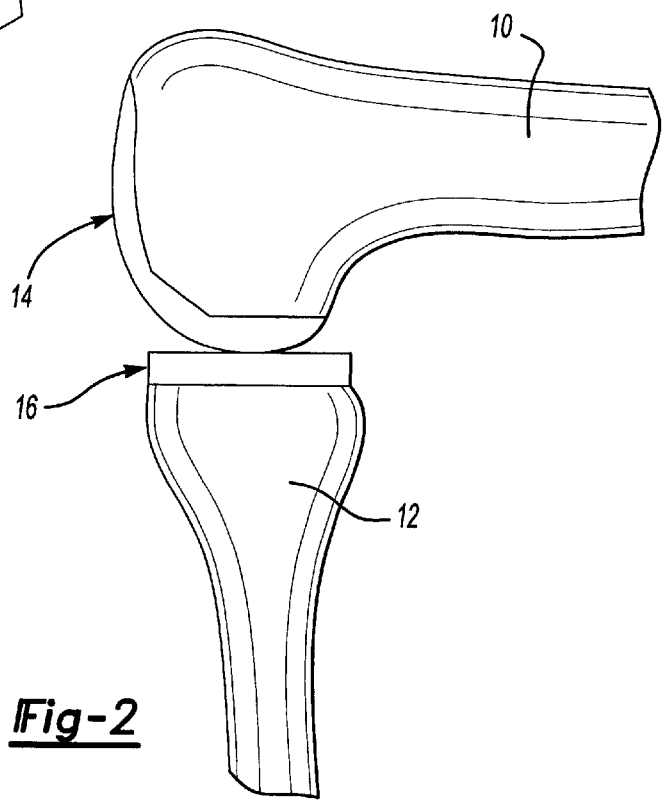
FIG. 2 is a medial view of an embodiment of the present invention implanted in a knee joint.
Figure 3:
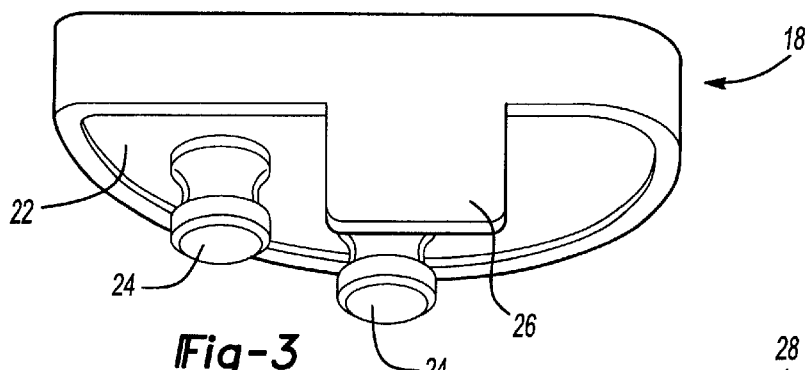
FIG. 3 is a perspective view of a right medial tibial tray of the present invention.
Figure 4:
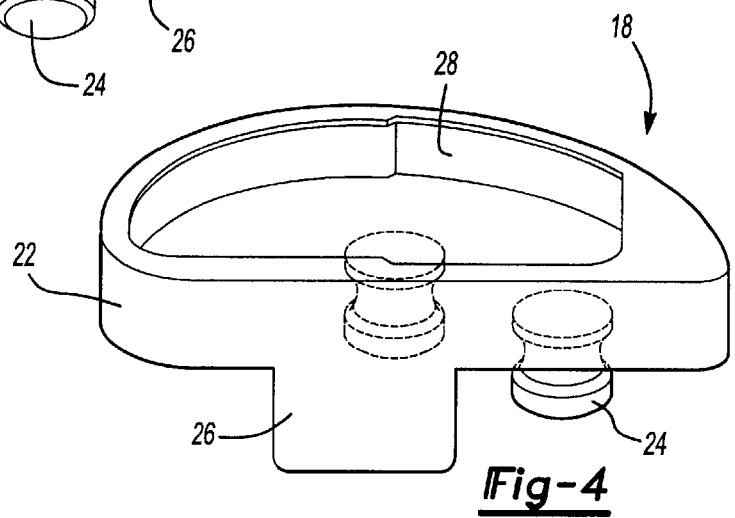
FIG. 4 is another perspective view of a right medial tibial tray of the present invention.
Figure 5:
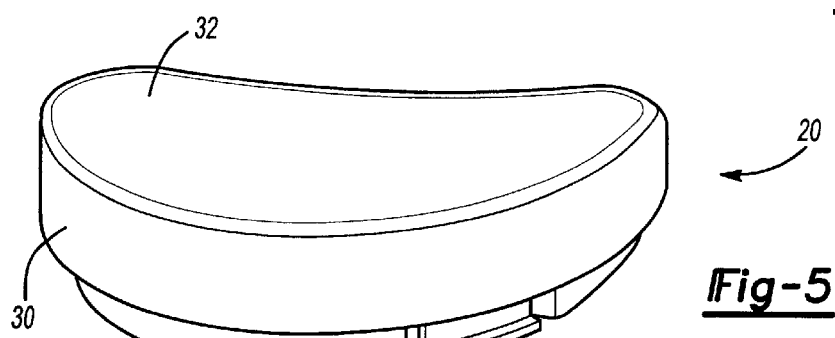
FIG. 5 is a perspective view of a right medial tibial insert of the present invention.
Figure 6:
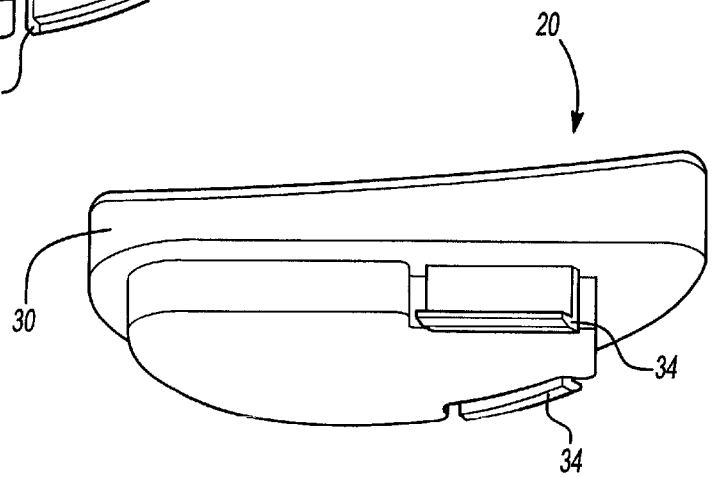
FIG. 6 is a another perspective view of a right medial tibial insert of the present invention.

Referring to FIGS. 1 and 2, a unicondylar knee prosthesis implanted using the instruments and method of the invention is shown. A femur 10 is shown in combination with a tibia 12. Femur 10 has a femoral component 14 implanted therein. Tibia 12 has a tibial component 16 implanted therein. While a right medial surgery is shown, it is known that the method will apply to both medial and lateral components, as well as left and right knees.

With reference to FIGS. 3–6, tibial component 16 includes a tibial tray 18 and a tibial insert 20. Tibial component 16 is designed to resurface the proximal end of the tibia to cooperate with a unicondylar femoral component 14. Tibial tray 18 includes a generally "D" shaped body 22 having a pair of posts 24 extending orthogonally therefrom. Tibial tray 18 also includes a tab 26 extending from body 22 in the same direction as posts 24. Body 22 includes a snap groove 28 configured to receive tibial insert 20. It should be appreciated that the two piece tibial component described is merely exemplary and that singular or other multi-piece designs are contemplated for use with the femoral component of the present invention.

Tibial insert 20 may be constructed from any suitable bearing material such as ultra high molecular weight polyethylene (UHMWPE). Tibial insert 20 includes a generally D-shaped body 30 having a wear surface 32. A pair of snap tabs 34 extend from the opposing surface of body 30. It should be appreciated that snap tabs 34 of tibial insert 20 engage snap groove 28 of tibial tray 18 once tibial component 16 is assembled. In this manner, a modular unicondylar tibial component may be implanted and subsequently reconstructed by removing only the wearable tibial insert 20. Accordingly, the tibial tray to tibia interconnection need not be disturbed.

Figure 7:
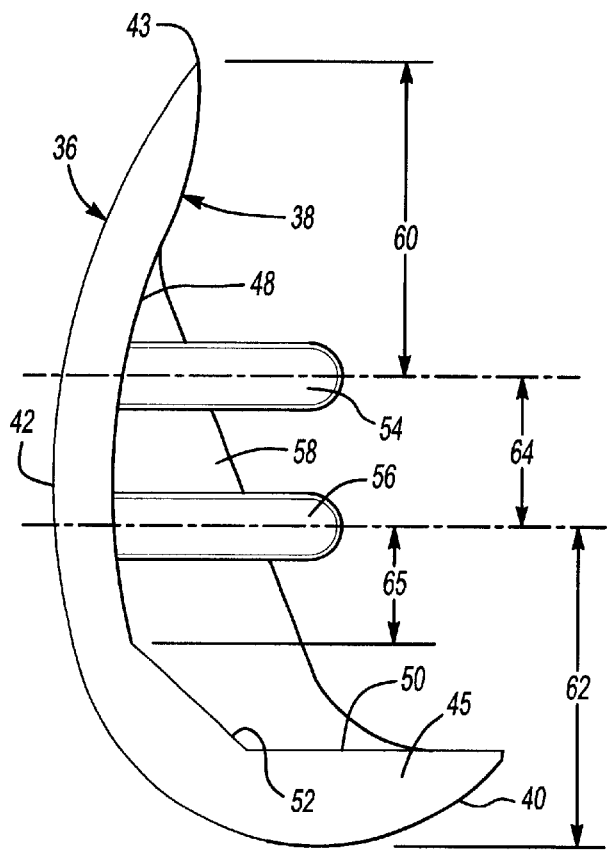
FIG. 7 is a lateral view of a femoral component of the present invention.
Figure 8:
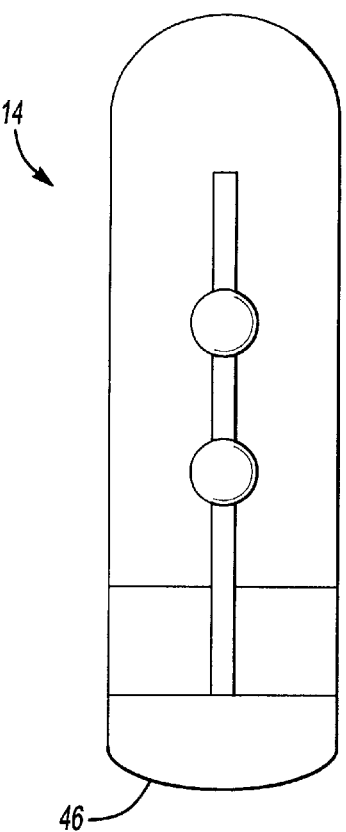
FIG. 8 is a superior view of a femoral component of the present invention.
Figure 9:
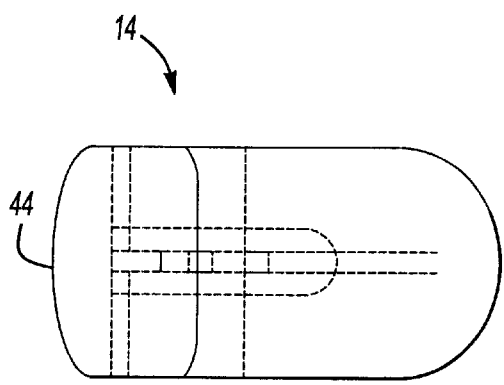
FIG. 9 is a posterior view of a femoral component of the present invention.
Figure 10:
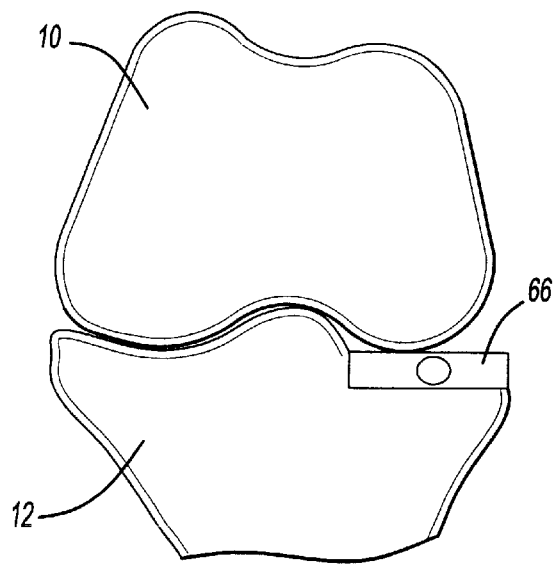
FIG. 10 is an anterior view of a spacer positioned within a tibial resection adjacent a femur.
Figure 11:
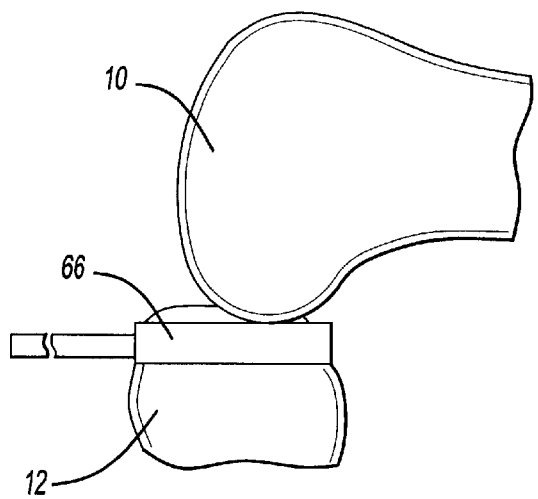
FIG. 11 is a medial view of a spacer positioned within a tibial resection adjacent a femur.
Figure 12:
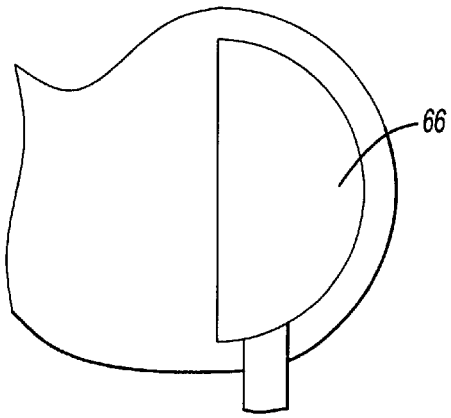
FIG. 12 is a superior view of the spacer placed within the tibial resection with the femur removed.
Figure 13:
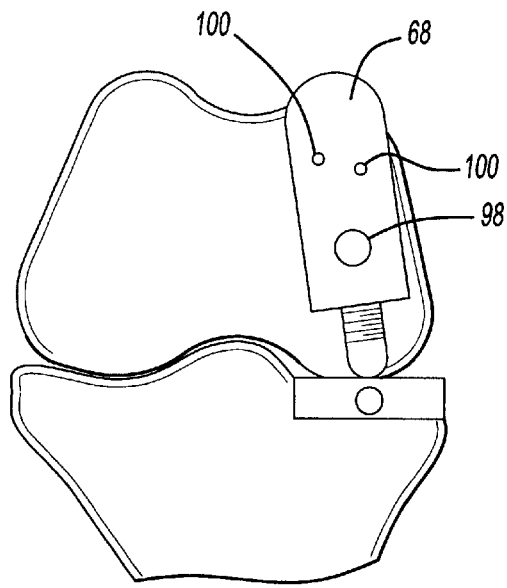
FIG. 13 is an anterior view of a femoral sizing guide placed on a femur acting in conjunction with the tibial spacer of the present invention for anterior referencing.

With reference to FIGS. 7–9, femoral component 14 is depicted in detail. Femoral component 14 is designed to resurface the distal and posterior portions of one of the femoral condyles of femur 10. Femoral component 14 has an articulating surface 36 and a bone mating surface 38. Articulating surface 36 in the preferred embodiment includes a pair of radial surfaces 40 and 42 that are tangent to one another forming a smooth flowing surface when viewed from the lateral direction. Radial surface 42 terminates at an anterior run-out 43 of femoral component 14. In the other plane (FIG. 9), the distal portion of femoral component 14 includes a radius 44 extending from anterior run-out 43 to a posterior portion 45 that is larger than and blends with a radius 46 that is present on posterior portion 45. This allows for more movement between femur 10 and tibia 12 when in flexion than in extension, similar to the natural knee.

Bone mating surface 38 is comprised of a distal surface 48, a posterior surface 50, and a posterior chamfered surface 52. Extending from bone mating surface 38 is a first peg 54 and a second peg 56. Pegs 54 and 56 aid in alignment and stability. Preferably, a rib 58 interconnects first peg 54 and second peg 56 to resist rotation of femoral component 14 after implantation.

First peg 54 is positioned a pre-determined distance 60 from anterior run-out 43. In addition, second peg 56 is positioned a pre-determined distance 62 from posterior portion 45. As will be described in greater detail hereinafter, distances 60 and 62 remain constant as femoral component size changes. A surgeon has the option of choosing anterior or posterior referencing while using a common femoral component. Accordingly, as the size of the femoral component increases, a distance 64 between first peg 54 and second peg 56 increases in order to maintain distances 60 and 62 constant.

It should be appreciated that the femoral component previously described as having both first and second pegs is merely exemplary. For example, another embodiment of a femoral component constructed in accordance with the teachings of the present invention includes a single peg positioned predetermined distance 60 from anterior run out 43. Similarly, another femoral component embodiment exists having a single peg positioned predetermined distance 62 from posterior portion 45. Therefore, alternate femoral component embodiments may be constructed by simply removing one of first peg 54 or second peg 56.

Another embodiment of the present invention positions first peg 54 a pre-determined distance 65 from chamfer 52. In this manner, the size and location of chamfer 52 are also standardized. One skilled in the art should appreciate that first peg 54 may also be positioned a constant distance from posterior surface 50 without departing from the scope of the present invention.

The method of implantation for the unicondylar knee prosthesis will now be described including a description of the instruments used for the method. With reference to FIGS. 10–14, the knee is articulated in flexion and an incision is made to open the knee as is known by those skilled in the art. After exposure of the joint, tibia 12 is resected using a tibial cutting guide (not shown). A tibial spacer 66 is inserted at the tibial resection. At this time, the surgeon determines the proper joint tension by articulating the joint through flexion and extension with spacer 66 in place. If the joint is too lax, a spacer having a greater thickness is inserted. Conversely, if the joint tension were too tight, a spacer having a lesser thickness would be inserted. Once the proper joint tension is set, the corresponding spacer remains positioned between the posterior distal femur and the tibial resection. Alternatively, the joint tension may be set using a tensioning device. The tensioning device (not shown) loads and positions femur 10 relative to tibia 12 to properly define the distance between resected tibia 12 and femur 10 without the use of spacer 66.

At this time, the surgeon must decide which referencing method is best suited for the patient. The anterior referencing method will be described first. Femur 10 is sized using a sizing guide 68. Sizing guide 68 includes a body 70 having a first portion 72 and a second portion 74. First portion 72 includes a peg aperture 76 and a pin aperture 78. Second portion 74 extends anterior of first portion 72. Second portion 74 includes a first face 80 and a second face 82 generally converging at a point 84.

Sizing guide 68 also includes an indexable probe 86. A sizing scale 88 is imprinted on an exterior surface of indexable probe 86. Indexable probe 86 has a first end 90 disposed within a probe aperture 92 located within first portion 72. Indexable probe 86 also includes a second end 94.

Figure 14:
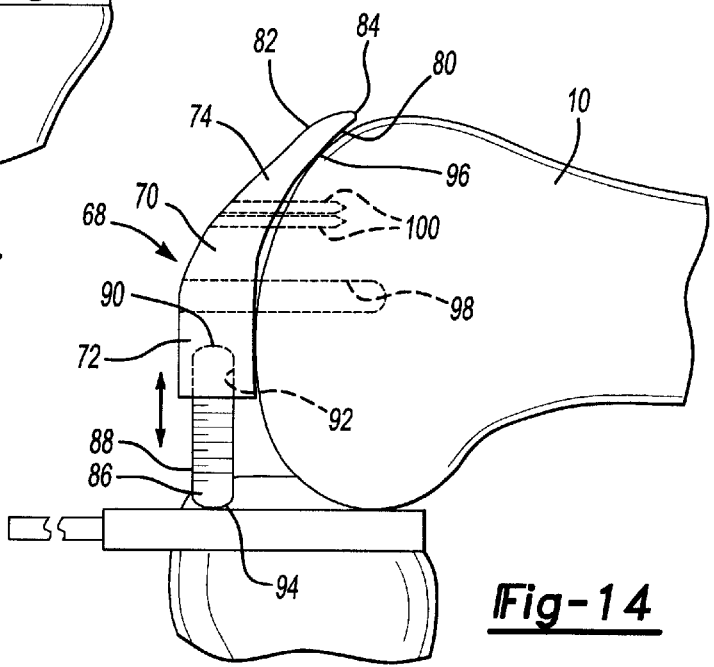
FIG. 14 is a medial view of a femoral sizing guide mounted on a femur acting in conjunction with a tibial spacer for anterior referencing.

To determine the proper femoral component size to be implanted, sizing guide 68 is placed over a distal end of femur 10 as shown in FIG. 14. Body 70 is aligned such that first face 80 contacts anterior reference point 96 at the edge of the anterior run-out. It should also be appreciated that sizing guide 68 is placed at a slight angle in relation to tibial spacer 66 along the line formed by the anterior and posterior portions of distal femur 10. Once aligned, sizing guide 68 is pinned in place while a first peg aperture 98 is drilled. Preferably, first pin apertures 100 are machined using relatively small, headless drill bits that are left in place to align sizing guide 68 and a resection guide as will described in greater detail hereinafter. Once sizing guide 68 has been aligned and pinned as previously discussed, indexable probe 86 is translated until second end 94 contacts tibial spacer 66. The size is determined by noting where sizing scale 88 meets first portion 72 of body 70. Sizing guide 68 is removed.

Figure 15:
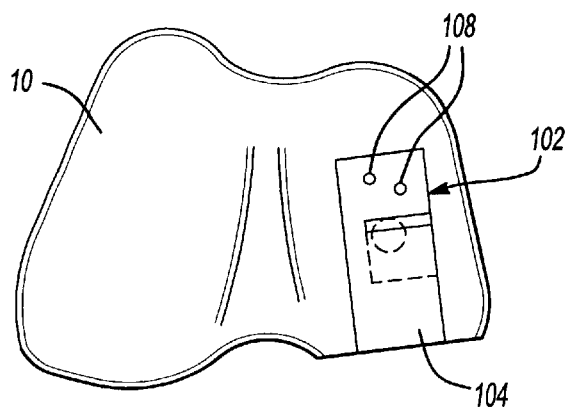
FIG. 15 is an anterior view of a posterior resection guide placed on a femur.
Figure 16:
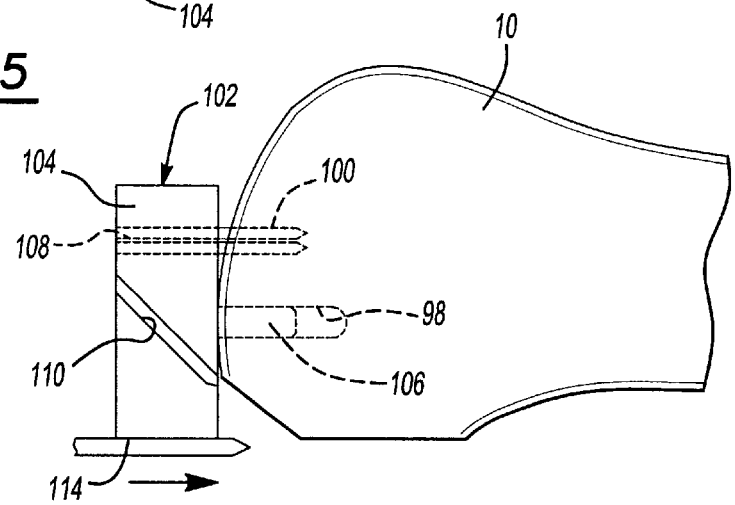
FIG. 16 is a medial view of a posterior resection guide placed on a femur.

With reference to FIGS. 15 and 16, an appropriately sized resection guide 102 is mounted to femur 10. Posterior resection guide 102 includes a generally rectangular body 104 having a peg 106 extending therefrom. Body 104 also includes at least one pin aperture 108 used to align resection guide 102 relative to femur 10. As mentioned earlier, in the preferred technique, the surgeon leaves the headless drill bit used to create first pin aperture 100 therewithin. Accordingly, proper alignment of posterior resection guide 102 is guaranteed by disposing peg 106 within first peg aperture 98 while disposing the headless drill bit within pin aperture 108.

Posterior resection guide 102 includes a slot 110 used to guide the saw blade when making the posterior chamfer cut. Body 104 includes a posterior surface 114 used to guide a saw blade when making the posterior cut. The posterior chamfer cut is designed to correspond to bone mating surface 52. The posterior cut acts in conjunction with bone mating surface 50. Posterior resection guide 102 may also include a second drill guide used to guide a drill for forming a second peg aperture (not shown) if desired. Alternatively, a separate drill guide may be introduced to align a drill bit when forming the second peg aperture.

Figure 17:
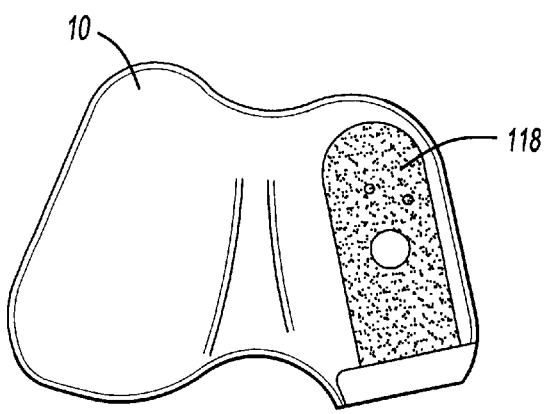
FIG. 17 is an anterior view of a femur depicting a distal femoral area of bone to be removed.
Figure 18:
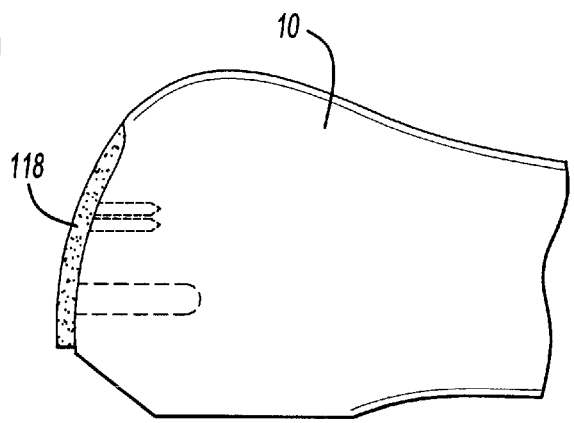
FIG. 18 is a medial view of a femur depicting a distal femoral area of bone to be removed prior to the implantation of the components of the present invention.

The posterior resection guide and headless drill bit are removed to perform a final bone removal step. As shown in FIGS. 17 and 18, a distal portion 118 is removed to correspond to distal surface 48 of femoral component 14. If the specific femoral component chosen includes rib 58, an additional cut is made in the distal femur to allow complete insertion of rib 58 within the cut.

To complete the unicondylar implantation process, femoral component 14 is cemented to femur 10. Similarly, tibial component 16 is cemented to tibia 12 using a conventional cementing technique that is well known to those skilled in the art. The wound is then closed and post-operative care is given.

As mentioned earlier, the present invention is directed to both anterior and posterior referencing methods and instruments. If the surgeon decides after initially opening the joint, that a posterior referencing method is more desirable than an anterior referencing method, a different procedure and set of instruments are used as described below.

Figure 19:
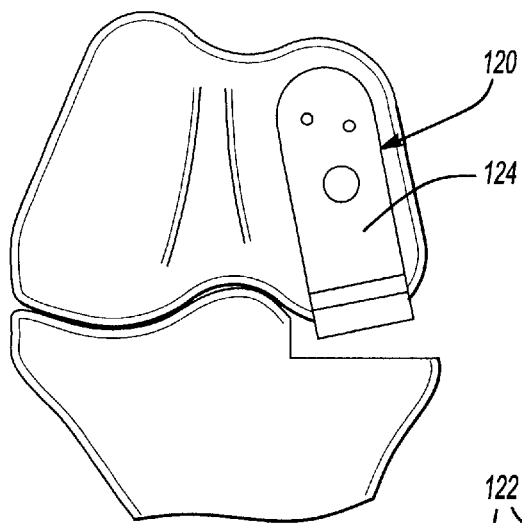
FIG. 19 is an anterior view of a posterior resection guide placed on a femur.
Figure 20:
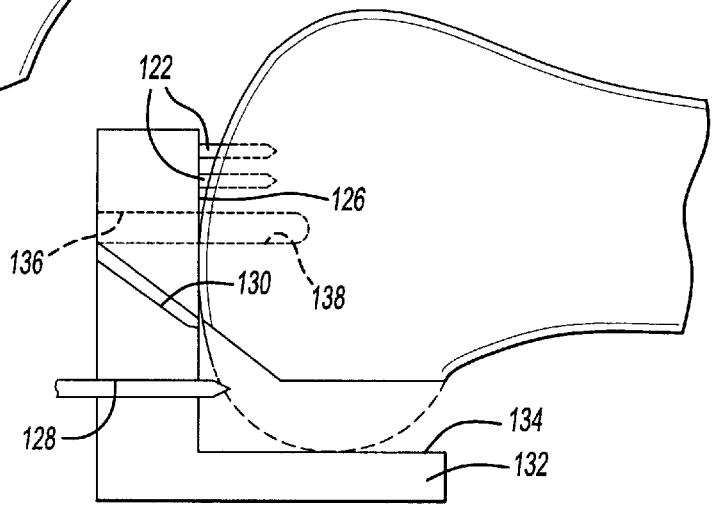
FIG. 20 is a medial view of a posterior resection guide placed on a femur.

As shown in FIGS. 19 and 20, the posterior referencing method begins by making a tibial resection as previously described in the anterior referencing method section. Next, a posterior resection guide 120 is coupled to femur 10 using pins 122. Pins 122, are preferably headless drill bits temporarily left in place to provide alignment for posterior resection guide 120. Posterior resection guide 120 includes a body 124 having a contact face 126 in contact with distal end of femur 10. Body 124 also includes a first slot 128 and a second slot 130 for guiding a saw blade. First slot 128 is used to create a posterior cut. Second slot 130 is useful when making a posterior chamfer cut. A leg 132 extends from guide 120 and includes a contacting surface 134 in contact with posterior femur 10. Posterior resection guide 120 also includes a first drill guide 136 for guiding a drill to create a first peg aperture 138.

Figure 21:
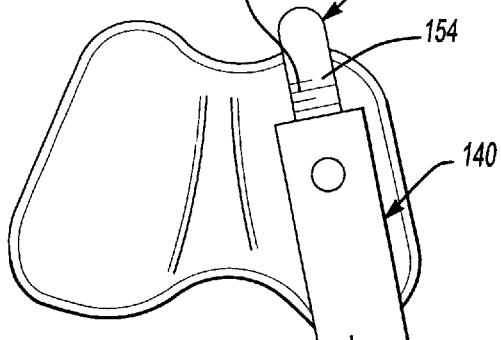
FIG. 21 is an anterior view of a femoral sizing guide placed on a femur for posterior referencing.
Figure 22:
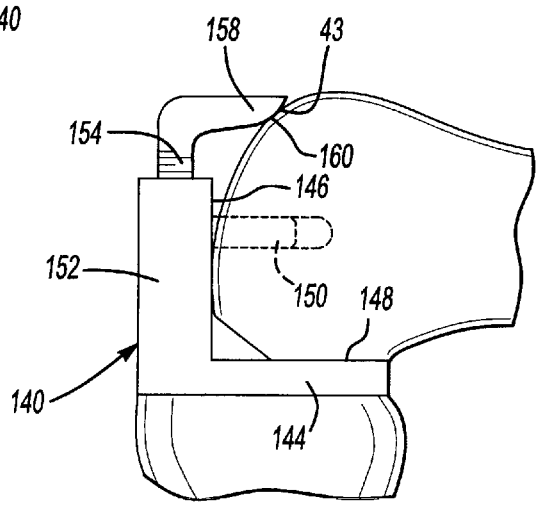
FIG. 22 is a medial view of a femoral sizing guide placed on a femur for posterior referencing.

After the posterior cut, posterior chamfer cut and first peg aperture are formed, posterior resection guide 120 is removed and a sizing guide 140 is placed on the distal femur as depicted in FIGS. 21 and 22. Sizing guide 140 includes a body 142 and an extending leg 144. Body 142 includes a face 146 in contact with the distal surface of the femur. Leg 144 includes a face 148 in contact with and positioned adjacent to the posterior cut. An alignment peg 150 extends from body 142 and is disposed within first peg aperture 138. An indexable probe 152 includes a shaft 154 slidably mounted within body 142. Shaft 154 has a graduated sizing scale 156 imprinted thereon indexable probe 152 also includes a finger 158 extending from shaft 154. Finger 158 includes a contact surface 160. To determine the correct femoral component size, indexable probe 152 is translated until contact surface 160 contacts an terior run-out 43 of femur 10. At this time, the surgeon reads graduated sizing scale 156 to determine the proper femoral component size.

After removal of sizing guide 140, a drill guide (not shown) is coupled to femur 10 to guide a bit to drill a second peg aperture if required. Lastly, distal bone portion 118 (FIG. 18) is removed as previously discussed. Both the femoral and tibial components are implanted and the wound is closed.

What is claimed is:

1. A set of femoral orthopedic devices comprising:
   a first component having a first size, said first component having a peg positioned predetermined distance from a first reference point, said first reference point selected from the group consisting of a point corresponding to a location on an anterior femoral condyle and a point corresponding to a location on a posterior femoral condyle; and
   a second component having a second size other than said first size, said second component having a peg positioned said predetermined distance from a corresponding reference point on said second component.

2. The set of orthopedic devices of claim 1 wherein said first reference point is an anterior run out of a femoral condyle.

3. The set of orthopedic devices of claim 1 wherein said first component includes a second peg positioned a second predetermined distance from a second reference point, said second component including a second peg positioned said second distance from said second reference point.

4. The set of orthopedic devices of claim 3 wherein said first reference point is located at an anterior run out of a femoral condyle and said second reference point is located at a posterior femoral condyle.

5. The set of orthopedic devices of claim 1 wherein said first and second components are unicondylar femoral implants.

6. The set of orthopedic devices of claim 1 wherein said first reference point is an anterior run out of a femoral condyle.

7. The set of orthopedic devices of claim 1 wherein said first component includes a second peg positioned a second predetermined distance from a second reference point, said second component including a second peg positioned said second distance from said second reference point.

8. The set of orthopedic devices of claim 7 wherein said first reference point is located at an anterior run out of a femoral condyle and said second reference point is located at a posterior femoral condyle.

9. A set of femoral orthopedic devices comprising:
   a first component having a first size, said first component having a first peg and a second peg, said first peg positioned a first predetermined distance from a first reference point, said second peg positioned a second predetermined distance from a second reference point; and
   a second component having a second size, said second component having a first peg positioned said first predetermined distance from said first reference point and a second peg positioned said second predetermined distance from said second reference point.

10. The set of orthopedic devices of claim 9 wherein said first reference point is a femoral condylar anterior run out.

11. The set of orthopedic devices of claim 10 wherein said second reference point is a femoral condylar posterior.

12. The set of orthopedic devices of claim 9 wherein a distance between said first and second pegs varies as said size varies.

13. The set of orthopedic devices of claim 9 wherein said first and second components are unicondylar femoral implants.

14. A method of implanting a femoral components on a femur, the method comprising:

referencing a femoral condyle at a first reference point, locating a peg aperture a predetermined distance from said first reference point, said peg aperture operable to receive a peg of said femoral component, selecting a sized femoral component, wherein the size of said femoral component is defined by a distance from said peg to a second reference point; and implanting said sized femoral component by disposing said peg within said peg aperture.

15. The method of claim 14 further including locating a second peg aperture in relation to said second reference point.

16. The method of claim 14 wherein said first reference point is a femoral condylar anterior run out.

17. The method of claim 14 wherein said second reference point is a femoral condylar posterior.

18. The method of claim 14 further includes resecting a portion of said femur to cooperate with said femoral component.

19. A set of femoral orthopedic devices comprising:
   a first component having a first size, said first component having a peg positioned a predetermined distance from a first reference point, said first reference point selected from the group consisting of a point on an anterior femoral condyle and a point on a posterior femoral condyle; and
   a second component having a second size other than said first size, said second component having a peg positioned said predetermined distance from said first reference point on the femoral condyle.

20. The set of orthopedic devices of claim 19 wherein said first and second components are unicondylar femoral implants.

* * * * *

UNITED STATES PATENT AND TRADEMARK OFFICE
CERTIFICATE OF CORRECTION

PATENT NO. : 6,494,914 B2  Page 1 of 1
DATED : December 17, 2002
INVENTOR(S) : David Ray Brown and Jacy Charles Hoeppner It is certified that error appears in the above-identified patent and that said Letters Patent is hereby corrected as shown below:

<u>Title page,</u>
Item [57], ABSTRACT,
Line 5, after "point" insert a period.

<u>Column 2,</u>
Line 10, after "point" insert a period.
Line 37, delete "a".

<u>Column 5,</u>
Line 20, after "will" insert -- be --.

<u>Column 6,</u>
Line 27, "thereon indexable" should be -- thereon. Indexable --.
Line 31, "an terior" should be -- anterior --.
Line 43, after "positioned" insert -- a --.

<u>Column 7,</u>
Line 35, "components" should be -- component --.

Signed and Sealed this

Twenty-fourth Day of June, 2003

JAMES E. ROGAN
*Director of the United States Patent and Trademark Office*